United States Patent [19]

Brown

[11] 3,989,799

[45] Nov. 2, 1976

[54] DIVALENT METAL SALTS OF DODECAMETAL TRIACONTA CARBONYLS

[75] Inventor: Earle S. Brown, South Charleston, W. Va.

[73] Assignee: Union Carbide Corporation, New York, N.Y.

[22] Filed: Mar. 27, 1974

[21] Appl. No.: 455,379

[52] U.S. Cl. .......................... 423/249; 260/429 R; 260/439 CY; 423/417
[51] Int. Cl.² ..................... C01F 13/00; C01G 1/04
[58] Field of Search .......................... 423/249, 417; 260/429 R, 439 CY

[56] References Cited
OTHER PUBLICATIONS

Chem. Abstracts 71:56181*t*.
Chem. Abstracts 71:117395*q*.
Chem. Abstracts 71:129672*r*.

*Primary Examiner*—Benjamin R. Padgett
*Assistant Examiner*—Deborah L. Kyle
*Attorney, Agent, or Firm*—George A. Skoler

[57] ABSTRACT

This invention relates to novel carbonyl mixed metal salts, containing more than one metal and having the formula:

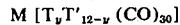

$$M [T_y T'_{12-y} (CO)_{30}]$$

wherein M is a divalent metal cation which is one of beryllium, magnesium, calcium, strontium, radium, manganese, iron, ruthenium, cobalt, nickel, palladium, platinum, zinc, cadmium, mercury, cerium and europium, T and T' are each different metals selected from the group consisting of cobalt, iridium and rhodium, and y may be any whole number between 1 and 11.

These compounds are useful catalysts in the reaction between carbon monoxide and hydrogen to produce oxygenated compounds such as methanol, ethylene glycol, glycerine and 1,2-propylene glycol.

28 Claims, No Drawings

DIVALENT METAL SALTS OF DODECAMETAL TRIACONTA CARBONYLS

This invention is concerned with the formation of new mixed metal triaconta carbonyl salt clusters which are useful catalysts in the synthesis of reaction products of carbon monoxide and hydrogen.

The mixed metal triaconta carbonyl divalent metal salts of this invention are particularly useful in the reaction between carbon monoxide and hydrogen to produce oxygenated compounds such as alkanols and alkane diols and triols, for instance, methanol, ethylene glycol, glycerine, and 1,2-propylene glycol. These mixed metal triaconta carbonyl salts may be used as catalysts in the process described in U.S. patent application Ser. No. 371,350, filed on June 19, 1973.

The new mixed metal triaconta carbonyl salt clusters of this invention are characterized by the formula:

$$M [T_y T'_{12-y}(CO)_{30}]$$

wherein M is a divalent metal cation which is one of beryllium, magnesium, calcium, strontium, radium, manganese, iron, ruthenium, cobalt, nickel, palladium, platinum, zinc, cadmium, mercury, cerium and europium, T and T' are different metals and each is one of cobalt, iridium and rhodium, and $y$ may be any whole number between 1 and 11.

P. Chini, in a review article entitled "The Closed Metal Carbonyl Clusters" published in Reviews (1968), Inorganica Chimica Acta, pages 31–50, states that a metal cluster compound is "a finite group of metal atoms which are held together entirely, mainly, or at least to a significant extent, by bonds directly between the metal atoms even though some non-metal atoms may be associated intimately with the cluster." The mixed metal carbonyl cluster compounds of this invention contain rhodium bonded to iridium or cobalt or iridium bonded to cobalt. The preferable mixed metal carbonyl cluster compounds of this invention are those which contain rhodium bonds, more preferably those which contain rhodium-iridium bonds. These compounds desirably contain carbon and oxygen in the form of carbonyl (—C—O), in which the carbonyl may be "terminal", "edge bridging" and/or "face bridging". They may also contain hydrogen and carbon in forms other than carbonyl. The following is a structure of the triaconta carbonyl cluster anions of this invention:

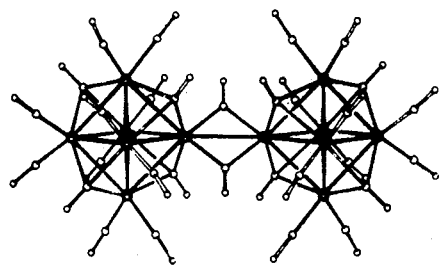

The structures of this invention are characterized by infrared analysis which shows four significant wave length bands in the metal carbonyl region in its infrared spectra at about 2070 cm$^{-1}$, about 2045 cm$^{-1}$, about 2008 cm$^{-1}$ and about 1773 cm$^{-1}$. Each of these bands may vary by ± 15 cm$^{-1}$.

The new triaconta carbonyl salts of this invention can be prepared from intermediate mixed metal dodecacarbonyl compounds having the formula $T_x T'_{4-x}(CO)_{12}$, wherein $x$ may have values from 1 to 3 and T and T' are different metals selected from the group of rhodium, cobalt and iridium.

The intermediate mixed metal dodecacarbonyl compounds used to prepare the triaconta carbonyl salt clusters of this invention may be prepared according to the methods disclosed in the paper entitled "New Mixed Tetranuclear Metal Carbonyls of Group VIIIB" by S. Martinengo, P. Chini, V. G. Abano, F. Cariati, and T. Salvatori, appearing in Journal of Organometallic Chemistry, 59(1973) pp. 379–394, C. Elsevier Sequoia S. A., Lausanne - Printed in The Netherlands, the disclosure of which is incorporated herein by reference.

Illustrative of procedures disclosed by Martinengo et al. for the preparation of the dodecacarbonyl compounds are the following.

A. A nucleophilic carbonyl of one transition metal attacking an electrophilic complex of a second transition metal (such as halide or carbonyl halide). This procedure must be conducted in a polar aprotic solvent under either an inert atmosphere (if the reactants contain sufficient carbon monoxide) or a carbon monoxide atmosphere. This is illustrated by the following equation:

$$2T(CO)_4^- + T'_2(CO)_4Cl_2 \rightarrow T_2T'_2(CO)_{12} + 2 Cl^-$$

B. Appropriate monomeric complexes (e.g. halides and carbonyl halides) of transition metals may be combined in aqueous solution under an atmosphere of CO. This is illustrated by the following equation:

$$xT(CO)_2Cl_2^- + (4-x)T'(CO)_3Cl_2 \rightarrow T_xT'_{4-x}(CO)_{12} + CO_2 + Cl^-$$

wherein $x$ may have values from 1 to 3.

The first procedure, A, will tend to yield single compounds while the second, B, will tend to give mixtures of compounds. These mixtures may be separated by appropriate means (e.g. chemical separation, liquid-solid chromatography such as where silica gel is the solid phase and non-polar organic liquids are the liquid phase) or may be used in subsequent steps as is.

The mixed metal triaconta carbonyl salts of this invention can be prepared by any one of the following procedures:

1. The mixed metal cluster, $T_x T'_{4-x}(CO)_{12}$, wherein $x$ has a value from 1 to 3, is contacted in an inert atmosphere with an excess of a soluble metal carboxylate of the desired metal cation in an appropriate solvent containing water in trace amounts up to 20% by weight of the solvent.

2. Alternatively, these compositions may be prepared by contacting under an atmosphere of carbon monoxide a mixture of monomeric transition metal carbonyl complexes with a soluble metal carboxylate in a suitable solvent containing water in trace amounts up to 20% by weight of the solvent.

3. These compositions can also be prepared via a double decomposition (or exchange) of an appropriate metal salt of the $[T_y T'_{12-y}(CO)_{30}]^=$ anion, in which the metal cation is different from the desired metal cation, by contacting the salt with a salt of the desired metal cation and carrying out the double decomposition (or exchange) in an appropriate solvent under an inert atmosphere.

If a single cluster compound of the formula, $T_xT'_{4-x}(CO)_{12}$, wherein $x$ may have values of 1 to 3, is used as a starting material in procedure 1, there will be obtained a single salt compound having an anion of the formula $$[T_yT'_{12-y}(CO)_{30}]^= \qquad (1)$$

in which case $y$'s value will be a number average value from 3 to 9. If a mixture of $T_xT'_{4-x}(CO)_{12}$ clusters is used as a starting material, a mixture of products will be expected. Where it is desirable to obtain cluster compounds of the above formula wherein $y$ has the extreme values of 1,2,10 and 11, the amount of single metal, which is in the maximum concentration, is added as a dodecacarbonyl cluster to the mixed metal dodecacarbonyl cluster in an amount sufficient to attain that concentration. This is illustrated by the following equations

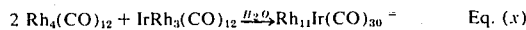  Eq. $(x)$

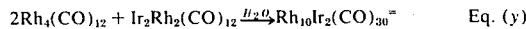  Eq. $(y)$

In equation $(x)$ rhodium has the maximum concentration in the mixed metal cluster and therefore the single metal rhodium cluster is added in a concentration sufficient to form the $Rh_{11}Ir(CO)_{30}{}^=$ anion. In equation $(y)$ where the concentration of each metal may be added in the required amount to form the desired anion where $y$ would have a value of 10 in Formula I, above, the addition of the single metal dodecacarbonyl cluster in procedure 1 above to obtain the extreme values of $y$ may also be made in procedure 2 above to obtain these same values of $y$. Cobalt compounds may be substituted for the rhodium or iridium compounds in equations $(x)$ and $(y)$.

Procedure 2 may be expected to yield a mixture of products while procedure 3 will yield either a mixture or a single product depending on the starting material.

It is believed that the above processes are achieving part or all of the reactions in the sequence depicted below:

$xT(CO)_n + (4-x)T'(CO)_mL_r \rightarrow T_xT'_{4-x}(CO)_{12}$ (a)

$xT(CO)_nL_s + (4-x)T'(CO)_pL'_e \rightarrow T_xT'_{4-x}(CO)_{12}{}^=$ (b)

$T_xT'_{4-x}(CO)_{12} + H_2O \rightarrow [T_xT'_{4-x}(CO)_{11}(COOH)]^-$ (c)

$[T_xT'_{4-x}(CO)_{11}(COOH)] \rightarrow [T_xT'_{4-x}(CO)_{11}H]^- + CO_2$ (d)

$[T_xT'_{4-x}(CO)_{11}H] \rightarrow [T_xT'_{4-x}(CO)_{11}]^= + BH^+$ (e)

$[T_xT'_{4-x}(CO)_{11}]^= + T_xT'_{4-x}(CO)_{12} \rightarrow [T_{2x}T'_{8-2x}(CO)_{22}]^=$ (f)

$[T_{2x}T'_{8-2x}(CO)_{22}]^= + T_xT'_{4-x}(CO)_{12} \rightarrow [T_{3x}T'_{12-3x}(CO)_{34}]^= + 2\ CO$ (g)

$[T_{3x}T'_{12-3x}(CO)_{34}]^= \rightarrow [T_{3x}T'_{12-3x}(CO)_{30}] + 4\ CO$ (h)

The subscripts in reactions $(a)$ through $(h)$, above, may have the following values:

$x$ may have any value from 1 to 3;

In reaction $(a)$ $m$ and $r$ are whole numbers the sum of which has a value from 4 to 6 and $n$ is a whole number that has a value from 4 to 6 and $m$ cannot be zero.

In reaction $(b)$, $n$, $s$, $p$ and $e$ are whole numbers where the sum of $n + s$ and the sum of $s + e$ have a value from 4 to 6. $n$ and $p$ must each be at least one.

From the above, it can be seen that the amount of T and T' in the final product is equal to the molar ratio of each as provided in the manufacture of that product.

For example, reaction $(a)$ is believed to depict process A above. Reaction $(b)$ is believed to depict process B above. Reactions $(c)$ through $(h)$ are believed to define the steps of process 1 above and reactions $(b)$ through $(h)$ are used in process 2. In process 3, the reaction is between only the metal salt and $[T_yT'_{12-y}(CO)_{30}]^=$.

In reactions $(a)$ and $(b)$ above, "L" can be any of the anions of the strong mineral acids ($Cl^-$, $SO_4{}^{-2}$, $PO_3{}^{-3}$, $NO_3{}^-$ and the like), a carboxylate, or an organic ligand such as a compound which contains at least one nitrogen atom (hereinafter called Lewis base nitrogen atom) and/or at least one oxygen atom (hereafter called Lewis base oxygen atom), said atoms possessing a pair of electrons available for the formation of coordinate bonds with rhodium. Desirably, the organic ligand contains at least two Lewis base nitrogen atoms, or at least two Lewis base oxygen atoms, or at least one Lewis base nitrogen atom plus at least one Lewis base oxygen atom, said atoms possessing a pair of electrons available for the formation of coordinate bonds with cobalt, rhodium and iridium, and said organic ligand forming with the metal per se a chelate structure. In suitable embodiments the organic ligands contain from 2 and upwards to 4 Lewis base atoms, preferably from 2 to 3 such atoms, and most preferably 2 Lewis base atoms. These organic ligands are said to be multidentate or polydentate, that is to say, such ligands are bidentate, tridentate, or quadridentate, depending on whether 2, 3, or 4 Lewis base atoms are involved in the formation of chelate structures with the metal per se.

Organic ligands which contain at least one Lewis base nitrogen atom will oftentimes hereinafter be referred to as "organic nitrogen ligands"; those ligands which contain at least one Lewis base oxygen atom will oftentimes be referred to as "organic oxygen ligands"; and those which contain at least one Lewis base nitrogen atom plus at least one Lewis base oxygen atom will oftentimes be referred to as "organic aza-oxa ligands".

Suitable organic nitrogen ligands most generally contain carbon, hydrogen, and nitrogen atoms. Suitable organic oxygen ligands most generally contain carbon, hydrogen, and oxygen atoms. Suitable organic aza-oxa ligands most generally contain carbon, hydrogen, oxygen, and nitrogen atoms. The carbon atoms can be acyclic and/or cyclic such as aliphatic, cycloaliphatic, aromatic (including fused and bridged) carbon atoms, and the like. Preferably, the organic ligands contain from 2 to 20 carbon atoms. The nitrogen atoms can be in the form of imino ($-N=$), amino

nitrilo ($N \equiv$), etc. Desirably, the Lewis base nitrogen atoms are in the form of imino nitrogen and/or amino nitrogen. The oxygen atoms can be in the form of groups such as hydroxyl (aliphatic or phenolic), carboxyl

carbonyloxy

oxy (—O—), carbonyl

etc., all of said groups containing Lewis base oxygen atoms. In this respect, it is the "hydroxyl" oxygen in the —COH group and the "oxy" oxygen in the

group that are the Lewis base atoms. The organic ligands may also contain other atoms and/or groups such as alkyl, cycloalkyl, aryl, chloro, thioalkyl, trialkylsilyl, and the like.

Illustrative organic nitrogen ligands include for instance the polyalkylene diamines, triamines and tetraamines, such as N,N,N',N'-tetramethylethylenediamine, N,N,N',N'-tetraethylethylenediamine, N,N,N',N'-tetra-n-propylethylenediamine, N,N,N',N-tetramethylmethylenediamine, N,N,N',N'-tetraethylmethylenediamine, and N,N,N',N'-tetraisobutylmethylenediamine; piperazine; the lower N-alkyl substituted piperazines such as N-methylpiperazine, N-ethylpiperazine, 2-methyl-N-methylpiperazine; 2,2'-dipyridyl, methyl-substituted 2,2'-dipyridyl, ethyl-substituted 2,2'-dipyridyl, 1,4-diazabicyclo [2.2.2]-octane, methyl-substituted, 1,4-diazabicyclo-[2.2.2] octane, purine, 2-aminopyridine, 2-(dimethylamino)pyridine, methyl-substituted 1,10-phenanthroline, 2-(dimthylamino)-6-methoxyquinoline, 7-chloro-1,10-phenanthroline, 4-triethylsilyl-2,2'-dipyridyl, 5-(thiopentyl)-1,10-phenanthroline, and the like.

Illustrative organic oxygen ligands include, by way of illustrations, glycolic acid, methoxyacetic acid, ethoxyacetic acid, diglycolic acid, thiodigylcolic acid, diethyl ether, tetrahydrofuran, dioxane, tetrahydropyan, pyrocatechol, citric acid, 2-methoxyethanol, 2-ethoxyethanol, 2-n-propoxyethanol, 2-n-butylethanol, 1,2,3-trihydroxybenzene, 1,2,4-trihydroxybenzene, 2,3-dihydroxynaphthalene, cyclohexane-1,2-diol, oxetane, 1,2-dimethoxybenzene, 1,2-diethoxybenzene, methyl acetate, ethanol, 1,2-dimethoxyethane, 1,2-diethoxyethane, 1,2-di-n-propoxyethane, 1,2-di-n-butoxyethane, pentane-2,4-dione, hexane-2,4-dione, heptane-3,5-dione, octane-2,4-dione, 1-phenylbutane-1,3-dione, 3-methylpentane-2,4-dione; alkylene and polyalkylene glycols such as ethylene glycol, propylene glycol, butylene glycol, di-,tri-and tetraethylene and propylene glycols, or their mono-and dialkyl ethers such as the mono-and dimethyl ethers of mono-, di-, tri-and tetra-ethylene and propylene glycol; and the like.

Illustrative organic aza-oxa ligands include for example, ethanolamine, diethanolamine, isopropanolamine, di-n-propanolamine, N-N-dimethylglycine, N,N-diethylglycine, iminodiacetic acid, N-methyliminodiacetic acid, N-methyldiethanolamine, 2-hydroxypyridine, methyl-substituted 2-hydroxypyridine, picolinic acid, methyl-substituted picolinic acid, nitrilotriacetic acid, 2,5-dicarboxypiperazine, N-(2-hydroxyethyl) iminodiacetic acid, ethylenediaminetetraacetic acid, 2,6-dicarboxypyridine, 8-hydroxyquinoline, 2-carboxyquinoline, cyclohexane-1,2-diamine-N,N,N',N'-tetraacetic acid, the tetramethyl ester of ethylenediaminetetraacetic acid, and the like.

Other organic compounds which form coordinate covalent association with cobalt, rhodium and iridium carbonyl compounds are useful ligands. They are from organic compounds which possess Lewis base nitrogen atoms and typically are composed of carbon, hydrogen and nitrogen. Illustrative of such compounds are, e.g., piperidine, 2-methylpiperidine, 3-methylpiperidine, pyridine, 2-methylpyridine, 4-ethylpiperidine, dibutylamine, methylamine, dodecylamine, morpholine, aniline, benzylamine, octadecylamine, naphthylamine, cyclohexylamine, and the like.

The enumerated processes can be operated in an inert atmosphere at temperatures ranging from about 0° to about 120° C, and preferably at ambient room temperature (about 25° C) up to about 100° C. The pressures employed are dependent upon the amount of carbon monoxide required to complete product formation. In the case of the process enumerated A, carbon monoxide pressure is not required, therefore the process can be carried out at atmospheric pressure or superatmospheric pressure. In process 2 carbon monoxide pressure is required since reaction (b) typically requires CO addition. Since reaction (h) does not require added CO, the process enumerated as 3 above does not require CO pressure. Where pressures greater than atmospheric are required, e.g. where the addition of carbon monoxide is required to prepare the particular dedecacarbonyl or triaconta carbonyl mixed metal salt cluster, pressures ranging from atmospheric to 25,000 psia, preferably from about 50 to about 10,000 psia may be employed. The additional required carbon monoxide may also be furnished by a decarbonylation of excess reactant.

The residence time of the reactions can be followed by taking periodic infrared spectra of samples of the reaction.

The reaction time varies with the process chose, the pressures employed, and the temperatures used, and the like considerations.

The inert atmosphere is any gaseous materials which do not interfere with the reaction(s), and e.g., includes nitrogen, argon, helium, krypton, neon, and the like. Most desirably the reactions should be conducted in the absence of oxygen and light if stable mixed metal triaconta carbonyl compounds are to be obtained.

In the practice of these processes, the solvents employable include, by way of example, saturated and aromatic hydrocarbons, e.g., hexane, octane, dodecane, naphtha, decalin, tetrahydronaphthalene, derosene, mineral oil, cyclohexane, cycloheptane, alkylcycloalkane, benzene, toluene, xylene, naphthalene, lene, alkylnaphthalene, etc.; ethers such as tetrahydrofuran, tetrahydropyran, diethyl ether, 1,2-dimethoxybenzene, 1,2-ethoxybenzene, the mono- and dialkyl ethers of ethylene glycol, of propylene glycol, of butylene glycol, of diethylene glycol, of dipropylene glycol, of dibutylene glycol, of triethyleneglycol, of tetraethylene glycol, of oxyethyleneoxypropylene glycol, such as the mono- and dimethyl ethers of di-, tri- and tetraethylene glycol, etc.; alkanols such as methanol, ethanol, propanol, isobutanol, 2-ethylhexanol, etc.; ketones such as acetone, methyl ethyl ketone, cyclohexanone, cyclopetanone, etc.; esters such as methyl acetate, ethyl acetate, propyl acetate, butyl acetate, methyl propionate, ethyl butyrate, methyl laurate, etc.; water; anhydrides, such as phthalic anhydride, acetic anhydride, etc.; and others. Tetrahydrofuran, and the mono- and dialkylethers of triethylene and tetraethylene glycol are preferred diluents.

The following procedures represent the best modes available for producing the intermediate dodecacarbonyl mixed metal salt products of this invention.

PROCEDURE I

Preparation of $Rh_3Ir(CO)_{12}$.

In a glass vessel equipped with magnetic stirrer bar dissolve 100 mg. NaCl in 20 ml. $H_2O$ and buble CO through the solution for 15. min. Add $Rh_2(CO)_4Cl_2$, [100 millimoles (mmol)], the $Ir_2(CO)_6Cl_2$ [160 mg., 0.24 mmol)] and stir with continuous CO sparge for at least 24 hours. Filter the resulting brown precipitate, redissolve in a minimum amount of hexane, and cool to $-70°$ to precipitate orange crystalline product. The mother liquor may be concentrated to yield a second crop. Total yield is 100–120 mg., 0.12–0.14 mmol, 25–30 mmol%, of $Rh_3Ir(CO)_{12}$ containing minor amounts of $Ir_2Rh_2(CO)_{12}$ and $Rh_4(CO)_{12}$. The kinetics of the reaction are such that the formation of $Rh_3Ir(CO)_{12}$ is favored over the formation of $Rh_2Ir_2(CO)_{12}$.

Instead of the carbonyl compounds, the reactants may be the metal halides or metal halide salts, e.g., $IrX_3$, $RhX_3$, $K_2IrX_3$, $K_2RhXCl_6$ where X is Cl, Br. or I, when a halogen acceptor (e.g. metal powders of Ag, Cu, Zn) is included in the reaction. Alcohols (e.g. methanol) may be used as solvents, as can other polar liquids (e.g. ketones, ethers, polyethers, etc.)

PROCEDURE II

Preparation of $Ir_2Rh_2(CO)_{12}$

To 15 ml. dry tefrahydrofuran saturated with CO is added $Ir_4(CO)_{12}(220$ mg., 0.2 mmol) and Na metal (460 mg., 20 mmol). The mixture is stirred 24 hours, then filtered. The filtrate is added to $Rh_2(CO)_4Cl_2$ (100 mg., 0.25 mmol) and stirred 2 hours. The resulting solution is filtered and passed through a short column of silica gel with hexane as eluent. From the resulting solution, after evaporation there is obtained yellow-orange crystals of $Ir_2Rh_2(CO)_{12}$.

In the above procedures, I and II, the solvent may be any polar aprotic liquid free of halogen atoms; e.g., ketones, ethers, etc. The reducing agent can be any alkali metal and any alkaline earth metal. Preferably the reducing agent is sodium metal. The iridium and rhodium compounds can include any combination of a compound which will form $Ir)CO)_4^-$ on reduction (e.g., $Ir_4(CO)_{12}$, $Ir_2(CO)_6Cl_2$) and a rhodium halide or carbonyl halide ($RhX_3$, $Rh_2(CO)_4X_2$) where X is chlorine, bromine or iodine, or a compound which will form $Rh(CO)_4^-$ on reduction ($Rh_2(CO)_4Cl_2$, $Rh_4(CO)_{12}$), etc. and an iridium halide or carbonyl halide $IrX_3$, $Ir_2(CO)_6X_2$) where X is chlorine, bromine or iodine.

Where it is desirable to substitute cobalt for either of the rhodium or iridium compounds any cobalt compound which will form $Co(CO_4)^-$ on reduction may be used. Suitable cobalt compounds include $Co_4(CO)_{12}$, $Co_2(CO)_8$, and the like.

The following table depicts the tetranuclear cluster intermediate dodecacarbonyl products of this invention, along with the modes used for their synthesis.

| Starting Materials | Reaction Time (hrs.) | Procedure | Product |
| --- | --- | --- | --- |
| $NaIr(CO)_4 + Rh_2(CO)_4Cl_2$ | 1 | I | $Ir_2Rh_2(CO)_{12}$ |
| $Ir_2(CO)_6Cl_2 + NaRh(CO)_2(Cl)_2$ | 24 | II | $IrRh_3(CO)_{12}$ |
| $Ir_2(CO)_6Cl_2 + NaRh(CO)_2Cl_2$ | 24 | II | $Ir_3Rh(CO)_{12}$ |
| $2NaCo(CO)_4 + Rh_2(CO)_4Cl_2$ | 1 | I | $Co_2Rh_2(CO)_{12}$ |
| $NaCo(CO)_4 + RhCl_3$ | 1 | I | $Co_3Rh(CO)_{12}$ |

The following procedures represent the preferred modes for producing the mixed metal triaconta carbonyl divalent salts of the present invention.

PROCEDURE III

Preparation of $CaIr_3Rh_9(CO)_{30}$ 0.13 millimoles (mmol) of $Rh_3Ir(CO)_{12}$, which contains minor amounts of $Ir_2Rh_2(CO)_{12}$ and $Rh_4(CO)_{12}$ and a trace amount of $Ir_3Rh(CO)_{12}$, is charged to a glass vessel equipped with a magnetic stirrer bar. The vessel is then evacuated to a pressure of 1 millimeter of mercury and nitrogen introduced for the purpose of creating an inert atmosphere, 3.5 milliliters (ml) of tetrahydrofuran (THF) that had been predried to remove any moisture is introduced into the reaction vessel and after stirring for a few seconds 15 microliters of water is introduced into the reaction vessel. After 15 minutes 10 ml of distilled water is added to the reaction vessel and then the product is filtered while being maintained under a nitrogen atmosphere. The filtrate, the reaction product in THF, is then treated with 1 ml. of a saturated solution of calcium acetate to prepare the calcium salt of the triaconta carbonyl mixed metal anion. The calcium salt is isolated from the THF by vacuum distillation. A fine violet crystalline product is obtained.

The compound is identified by the appearance of a major peak at 2040 $cm^{-1}$, minor peaks at 2055 and $1775^{-1}$, and a deep purple coloration of the solution. Its nominal formula is $Ca\ Rh_9Ir_3(CO)_{30}$ but it undoubtedly also contains compounds of the formula $Ir_nRh_{12-n}(CO)_{30}$, where $n$ may have any value from 0 to 6, in minor and trace amounts.

The calcium salt of the triaconta carbonyl compound prepared in Procedure III is dissolved in 4 ml. of THF and then placed under 1 atmosphere of carbon monoxide pressure and allowed to remain there overnight. An infrared spectrum of the deep red THF solution shows that the triaconta carbonyl anion undergoes what is believed to be the following reaction

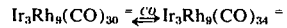

as evidenced by the appearance of three intense absorbance bands at about 1868, 1838 and 1785 $cm^{-1}$, in it's infrared spectrum. These absorbance bands may vary between about plus and minus 10 $cm^{-1}$ depending upon operating conditions and reactants.

PROCEDURE IV

In an inert atmosphere, $N_2$, the sodium salt of the dodecanuclear cluster anion, $Ir_3Rh_9(CO)_{30}^=$ (1.06 grams, 0.0005 moles) is dissolved in 70 ml. of distilled water at 25° C. To this solution is added 0.0015 moles of the divalent metal salt magnesium acetate. The insoluble divalent magnesium salt, having the formula, Mg[Rh$_9$Ir$_3$(CO)$_{30}$], is recovered by filtration under a nitrogen atmosphere.

The examples in the following table depict the preparation of typical dodecanuclear mixed metal triaconta carbonyl clusters of the present invention as made according to the methods in procedures III and IV, above.

TABLE

| Ex. | Starting Materials | Procedure | Reaction Time, Hours. | Product |
|---|---|---|---|---|
| 1 | CoRh$_3$(CO)$_{12}$ + Ca(OCOCH$_3$)$_2$ | III | 3 | Ca [Co$_3$Rh(CO)$_{30}$] |
| 2 | Co$_2$Ir$_2$(CO)$_{12}$ + Mg(NO$_3$)$_2$ | III | 2 | Mg [Co$_6$Ir$_6$(CO)$_{30}$] |
| 3 | Ir$_2$Rh$_2$(CO)$_{12}$ + Ca(NO$_3$)$_2$ | III | 2 | Ca [Ir$_6$Rh$_6$(CO)$_{30}$] |
| 4 | IrRh$_3$(CO)$_{12}$ + Sr(OCOCH$_3$)$_2$ | III | 3 | Sr [Ir$_3$Rh$_9$(CO)$_{30}$] |
| 5 | Ir$_2$Rh$_2$(CO)$_{12}$ + Mg(OCOCH$_3$)$_2$ | III | 3 | Mg [Ir$_6$Rh$_6$(CO)$_{30}$] |
| 6 | Na$_2$[Ir$_6$Rh$_6$(CO)$_{30}$] + Sr(NO$_3$)$_2$ | IV | 0.5 | Sr [Ir$_6$Rh$_6$(CO)$_{30}$] |

The dodecanuclear mixed metal triaconta carbonyl salt clusters prepared above are useful as catalysts in the reaction of the oxides of carbon and hydrogen to produce alkane diols and triols and their ether, ester and oligomer derivatives, particularly ethylene and propylene glycol and glycerine. The exact mechanism by which the triaconta carbonyl compounds act to catalyze the reaction is not fully appreciated at this time.

In using the mixed metal triaconta carbonyl salt clusters of this invention as a catalyst for the reaction of carbon monoxide and hydrogen to produce alkane diols and triols, having from 2 to 4 carbon atoms, the quantity of catalyst employed is not narrowly critical and can vary over a wide range. In general, the novel process is desirably conducted in the presence of a catalytically effective quantity of the active mixed metal species which gives a suitable and reasonable reaction rate. Reaction proceeds when employing as little as about $1 \times 10^{-6}$ weight percent, and even lesser amounts, of mixed metal based on the total weight of reaction mixture. The upper concentration limit can be quite high, e.g., about thirty weight percent of the mixed metal, and higher, and the realistic upper limit in practicing the process appears to be dictated and controlled more by economics in view of the exceedingly high cost of rhodium, iridium and cobalt metals and compounds. No particular advantages at the relatively high concentrations of catalyst are manifest. Depending on various factors such as the counter-ion of choice, the partial pressures of oxides of carbon and hydrogen, the total operative pressure of the system, the operative temperature, the choice of the normally-liquid organic diluent, and other considerations, a catalyst concentration of from about $1 \times 10^{-5}$ to about $1 \times 10^{-1}$ weight percent metal (contained in the complex catalyst) based on the total weight of reaction mixture, is generally desirable in the practice of the process.

The operative temperature which may be employed can vary over a wide range of elevated temperatures. In general, the process can be conducted at a temperature in the range of from about 100° C. and upwards to approximately 375° C. and higher. Operative temperatures outside this stated range, though not excluded from the scope of the invention, do not fall within certain desirable embodiments of the process. At the lower end of the temperature range, and lower, the rate of reaction to desired product becomes markedly slow. At the upper temperature range, and beyond, signs of some catalyst instability are noted. Notwithstanding this factor, reaction continues and polyhydric alcohols and/or their derivatives are produced. Additionally, one should take notice of the equilibrium reaction for forming ethylene glycol:

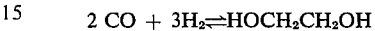

$$2\ CO + 3H_2 \rightleftharpoons HOCH_2CH_2OH$$

At relatively high temperatures the equilibrium increasingly favors the left hand side of the equation. To drive the reaction to the formation of increased quantities of ethylene glycol, higher partial pressures of carbon monoxide and hydrogen are required. Processes based on correspondingly higher operative pressures, however, do not represent preferred embodiments of the process in view of the high investment costs associated with erecting chemical plants which utilize high pressure utilities and the necessity of fabricating equipment capable of withstanding such enormous pressures. Suitable operative temperatures are between about 150° to about 300° C., and desirably from about 190° to about 275° C.

The process is suitably effected over a wide superatmospheric pressure range. At pressures below about 500 psia, the rate of desired product formation is quite slow, and consequently, relatively faster reaction rates and/or higher conversions to the desired product can be obtained by higher operative pressures, e.g., at a pressure of at least about 800 psia. Pressures as high as 50,000 psia, and higher, can be employed but with no apparent advantages attendant thereto which offset the unattractive plant investment outlay required for such high pressure equipment. In one embodiment of the process, the upper pressure limitation is approximately 25,000 psia. Effecting the novel process below about 14,000 psia, especially below about 6,000 psia, results in cost advantages which are associated with low pressure equipment requirements. A suitable pressure range is from about 1,000 psia to about 12,000 psia. The pressures referred to above represent the total pressure of hydrogen and oxides of carbon. In a preferred embodiment of the process, carbonyl complex catalyst is maintained in solution in the liquid reaction medium.

The process is effected for a period of time sufficient to produce the desired polyfunctional oxygencontaining products and/or derivatives thereof. In general, the residence time can vary from minutes to several hours, e.g., from a few minutes to approximately 24 hours, and longer. It is readily appreciated that the residence period will be influenced to a significant extent by the reaction temperature, the concentration and choice of the catalyst, the total gas pressure and the partial pressure exerted by its components, the concentration and choice of diluent, and other factors. The synthesis of the desired product(s) by the reaction of hydrogen with an oxide of carbon is suitably conducted under operative conditions which give reasonable reaction rates and/or conversions.

The relative amounts of oxide of carbon and hydrogen which are initially present in the reaction mixture can be varied over a wide range. In general, the mole ratio of CO:H$_2$ is in the range of from about 20:1 to about 1:20, suitably from about 10:1 to about 1:10, and preferably from about 5:1 to about 1:5. It is to be understood, however, that molar ratios outside the aforestated broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the process. For instance, polyhydric alcohols are obtained by using mixtures containing carbon dioxide and hydrogen. Mixtures of carbon dioxide, carbon monoxide and hydrogen can also be employed. If desired, the reaction mixture can comprise steam and carbon monoxide.

The process can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "run-away" reaction temperatures due to the exothermic nature of the reaction. In preferred embodiments of the process, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art. The catalyst may be initially introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the process especially to maintain the desired molar ratios of and the partial pressures exerted by the reactants.

As intimated previously, the operative conditions can be adjusted to optimize the conversion of the desired product and/or the economics of the process. In a continuous process, for instance, when it is preferred to operate at relatively low conversions, it is generally desirable to recirculate unreacted synthesis gas with/without make-up carbon monoxide and hydrogen to the reactor. Recovery of the desired product can be achieved by methods well-known in the art such as by distillation, fractionation, extraction, and the like. A fraction comprising catalyst, generally contained in byproducts and/or normally-liquid organic diluent, can be recycled to the reaction zone, if desired. All or a portion of such fraction can be removed or recovery of the catalyst values or regeneration to the active catalytic species, if necessary. Fresh mixed metal catalyst can be intermittently added to the recycle stream or directly to the reaction zone.

Either heterogeneous or homogeneous reaction mixtures may be employed in the practice of the process. In preferred embodiments, the catalysts as defined herein which are soluble in the reaction medium give outstanding results. However, the synthesis of polyhydric alcohols and/or derivatives thereof can be suitably effected by using such catalysts which are not homogeneously distributed throughout the reaction mixture. Solid catalysts which remain in place during the course of the reaction may be employed. Suspensions of liquid or solid catalysts in liquid and/or gaseous media may be employed. In suitable embodiments of the process the mixed metal catalyst can be used in combination with inert materials or contained or deposited on porous supports such as aluminia, silica-alumina, silica gel, activated charcoal, titania, zirconia, zeolites as well as the zeolitic molecular sieves, pumice, kiesel-guhr, inert porous organic polymers, (e.g., reticulated cation exchange resin) and the like.

Solutions of the novel catalytically active mixed metal carbonyl compounds can be deposited on porous carriers or supports of the type illustrated previously. For example, the catalytically active solution can be poured on the carrier, or the carrier can be immersed in an excess of the liquid solution, with the excess being subsequently removed. The impregnated support or carrier is then maintained at a temperature sufficient to volatilize the diluent to permit drying of the impregnated carrier. A vacuum may also be applied.

In the practice of preferred embodiments of the process a normally liquid organic diluent is employed. Such diluents can be inert organic diluents, or they may be reactive diluents, and they can include the aforedescribed organic ligands, or mixtures thereof. Illustrative of the normally-liquid organic diluents which are generally suitable in the practice of desirable embodiments of the invention include, for example, saturated and aromatic hydrocarbons, e.g., hexane, octane, dodecane, naphtha, decalin, tetrahydronaphthalene, kerosene, mineral oil, cyclohexane, cycloheptane, alkylcycloalkane, benzene, toluene, xylene, naphthalene, alkylnaphthalene, etc.; ethers such as tetrahydrofuran, tetrahydropyran, diethyl ether, 1,2-dimethoxybenzene, 1,2-ethoxybenzene, the mono- and dialkyl ethers of ethylene glycol, of propylene glycol, of butylene glycol, of diethylene glycol, of dipropylene glycol, of triethylene glycol, of tetraethylene glycol, of dibutylene glycol, of oxyethyleneoxypropylene glycol, etc., carboxylic acids such as acetic acid, propionic acid, butyric acid, caproic acid, stearic acid, benzoic acid, cyclohexanecarboxylic acid, etc.; alkanols such as methanol, ethanol, propanol, isobutanol, 2-ethylhexanol, etc.; ketones such as acetone, methyl ethyl ketone, cyclohexanone, cyclopentanone, etc.; esters such as methyl acetate, ethyl acetate, propyl acetate, butyl acetate, methyl acetate, ethyl acetate, propyl acetate, butyl acetate, methyl propionate, ethyl butyrate, methyl laurate, etc.; water; anhydrides such as phthalic anhydride, acetic anhydride, etc.; and others. Tetrahydrofuran, dioxane, and the mono and dialkylethers of triethylene and tetraethylene glycol are preferred diluents. More preferably, the diluents are the mono- and dimethyl ethers of tetraethylene glycol. It should be noted that the use of reactive diluents in the practice of desirable embodiments of the process can give rise to a range of useful products. For instance, the mono- and diacetate esters of ethylene glycol can be obtained by using acetic acid as the diluent in the reaction medium. The use of alkanols, e.g., methanol and ethanol, can result in the monoalkyl ethers of ethylene glycol.

In a further preferred embodiment of the process the triaconta carbonyl mixed metal divalent salt clusters that contain rhodium bonds, more preferably rhodium bonded to iridium, in the mixed metal part of the cluster, are employed as the catalysts.

The mixed metal clusters of this invention can have any of the ligands, listed in defining "L" in reactions (a) and (b) above, in "complex" combination with the mixed metal carbonyl cluster anions.

The term "complex" means a coordination compound formed by the union of one or more electronically rich molecules or atoms capable of independent existence with one or more electronically poor molecules or atoms, each of which is also capable of independent existence. These organic mixed-metal cluster complexes are derived from the association of organic ligands with the mixed metal carbonyl solutions.

In a specific illustration of the process one may use a 100 ml. capacity stainless-steel reactor capable of withstanding pressures up to 7000 atmospheres. It may be charged with 0.5 parts of the above catalysts dissolved in 45 parts of tetrahydrofuran. Then the reactor would be sealed and charged with, e.g., 1300 atmospheres of synthesis gas (mixture of hydrogen and carbon monoxide whose molar ratio may be $H_2:CO = 1:1$). Then the temperature of the reactor and its contents would be raised to, e.g., 220° C. Additional synthesis gas then would be added to bring the total pressure of the reactor and its contents to be, e.g., 3,400 atmospheres. If desired, additional synthesis gas may be supplied periodically to maintain the total pressure at 3,400 atmospheres. Then the reactor would be maintained at the desired pressure and temperature for a time, e.g., 5 hours, sufficient to produce ethylene glycol. Then the reactor and its contents would be cooled to room temperature and the excess gasses and reaction product would be discharged. Analysis of the reaction product may be made by gas-liquid chromatography.

What is claimed is:

1. Mixed metal triaconta carbonyl salts of the formula:

$$M[T_yT'_{12-y}(CO)_{30}]$$

wherein M is a divalent metal cation selected from the group consisting of beryllium, magnesium, calcium, strontium, radium, manganese, iron, ruthenium, cobalt, nickel, palladium, platinum, zinc, cadmium, mercury, cerium and europium, T and T' are each different metals selected from the group consisting of cobalt, iridium and rhodium, and y may be any whole number between 1 and 11.

2. The salt of claim 1 wherein M is beryllium.
3. The salt of claim 1 wherein M is magnesium.
4. The salt of claim 1 wherein M is calcium.
5. The salt of claim 1 wherein M is strontium.
6. The salt of claim 1 wherein M is radium.
7. The salt of claim 1 wherein M is manganese.
8. The salt of claim 1 wherein M is iron.
9. The salt of claim 1 wherein M is ruthenium.
10. The salt of claim 1 wherein M is cobalt.
11. The salt of claim 1 wherein M is nickel.
12. The salt of claim 1 wherein M is palladium.
13. The salt of claim 1 wherein M is platinum.
14. The salt of claim 1 wherein M is zinc.
15. The salt of claim 1 wherein M is cadmium.
16. The salt of claim 1 wherein M is mercury.
17. The salt of claim 1 wherein M is cerium.
18. The salt of claim 1 wherein M is europium.
19. The salt of claim 1 wherein T and T' are rhodium and iridium.
20. The salt of claim 19 having the formula $$M[Rh_9Ir_3(CO)_{30}]$$

21. The salt of claim 20 wherein M is calcium.
22. The salt of claim 20 wherein M is magnesium.
23. The salt of claim 19 having the formula $$M[Rh_6Ir_6(CO)_{30}]$$

24. The salt of claim 23 wherein M is calcium.
25. The salt of claim 23 wherein M is magnesium.
26. The salt of claim 1 wherein T and T' are rhodium and cobalt.
27. The salt of claim 26 having the formula $$M[Rh_9Co_3(CO)_{30}].$$

28. The salt of claim 27 wherein M is calcium.

* * * * *